United States Patent [19]

Miwa et al.

[11] Patent Number: 4,723,553
[45] Date of Patent: Feb. 9, 1988

[54] ULTRASOUND MEDIUM CHARACTERISTICS MEASURING APPARATUS

[75] Inventors: Hirohide Miwa; Keiichi Murakami; Akira Shiba, all of Kawasaki; Takaki Shimura, Machida; Hajime Hayashi, Yamato, all of Japan

[73] Assignee: Fujitsu Limited, Kawasaki, Japan

[21] Appl. No.: 878,858

[22] Filed: Jun. 26, 1986

[30] Foreign Application Priority Data

Jun. 26, 1985 [JP] Japan .................. 60-139521

[51] Int. Cl.$^4$ .............................................. A61B 10/00
[52] U.S. Cl. ............................................ 128/660; 73/602
[58] Field of Search .............. 369/415, 514, 517, 724; 73/599; 128/660-661

[56] References Cited

U.S. PATENT DOCUMENTS 4,545,250 10/1985 Miwa ........................... 73/599 X
4,648,276 3/1987 Klepper et al. ................. 73/599

OTHER PUBLICATIONS

Childers, D. G. et al., "The Cepstrum: A Guide to Processing", Proceedings of the IEEE, vol. 65, No. 10, Oct. 1977, pp. 1428–1443.
Jones, J. P. et al., "Ultrasonic Tissue Characterization: A Review", Acta Electronica, vol. 26, 190 1-2, 1984, pp. 3–31.
Hoshino, H. et al., "Microprogrammable Ultrasonic Image Processor and Its Applications to Image Manipulation", Proceedings of Society Photo-Opt. Instrumentation in Engineering, SPIE, vol. 314, Digital Radiography, (1981), pp. 354–361.
Sommer, G. et al., "Ultrasonic Characterization of Abdominal Tissues via Digital Analysis of Backscattered Waveforms", Radiology, vol. 141, No. 3, pp. 811–817, Dec. 1981.
Ophir, J. et al., "Attenuation Estimation in Reflection: Progress and Prospects, Ultrasonic Imaging, vol. 6, pp. 349–395, (1984).
Hohne, K. H. (ed), Digital Image Processing in Medicine, Springer-Verlag, publ. 1981, N.Y., pp. 160–166.
Ito, K. et al., "C-Mode Scan and Resolution Improvement Techniques for Ultrasonic Diagnosis", IEEE BME Transactions, vol. BME-26, No. 1, Jan. 1979.

Primary Examiner—Francis J. Jaworski
Attorney, Agent, or Firm—Staas & Halsey

[57] ABSTRACT

An apparatus for measuring acoustic characteristic values of a medium by sending ultrasound pulses into the medium and analyzing the reflected waves from the medium. Medium characteristic values are extracted from the reflected waves, and spectrum scalloping is eliminated. The present invention executes the nonlinear filtering process, for example, the median filtering process to the spectrums, applies a model spectrum to the filtered result and thereby facilitates measurement of suppressing fluctuation even when a small number of space average samples one used, by obtaining $\beta$ from such model spectrum.

7 Claims, 16 Drawing Figures

ULTRASOUND MEDIUM CHARACTERISTICS MEASURING APPARATUS

FIELD OF THE INVENTION

The present invention relates to an apparatus which measures acoustic characteristic values of a medium by sending ultrasound pulses to the medium and analyzing the reflected signals, and more specifically to a processing system for extracting medium characteristic value by eliminating the influence of spectrum scallop resulting from random reflectors in the logarithmic value of the spectrum of a reflected signal reflected from the measuring region.

BACKGROUND ART

The conventional ultrasound medium characteristic measuring apparatus utilizes dependency on frequency of attenuation and reflection. For example, when measuring living body tissue the received reflected wave, in the frequency domain is often analyzed.

A reflection signal corresponding to a minute region (3~10 mm) between the depths $z_1$ and $z_1 + \Delta z$ (FIG. 1) is extracted with a time gate from a series of reflection signals. The reflected signals are obtained by sending the ultrasound pulse, with a center frequency of 2~10 MHz and pulse length (duration) of about 1 μs, into a medium from the surface of the medium. Pulses reflected from respective depths of the medium are received and such reflected signals are analyzed as an echo signal, indicating tissue characteristics of the depth $z_1$. The depth z and time unit t of the reflected signal are related to the velocity of sound C of medium and expressed by the following equation:

$$t = 2z/C$$

An echo signal is converted to a power spectrum S(f) in the frequency domain by Fourier transform means, such as an FFT (Fast Fourier Transformer). Generally, many reflectors exist within the small domain and the reflected pulses from respective reflectors are superposed on each other and interfere with each other. Thus, the echo signal has a complicated waveform and its power spectrum takes a form where a spectrum $|R(f)|^2$, which can be seen as noise having random unevenness, is multiplied to the spectrum $S_0(f)$ of a reflected wave having a unit intensity reflected from one reflector. This concept is discussed dependent reflection factors in ultrasonic bio-tissue characterization" Proc. 1984 International Symp. on noise and clutter rejection in radars and imaging sensors. pp. 158–163, October 1984. This random spectrum $|R(f)|^2$ is called a scallop power spectrum and is expressed as the following equation (1):

$$|R(f)|^2 = R_0^2 (1 + \delta_{(f)}) \quad (1)$$

$R_0^2$ is a power reflection intensity of the entire part of the small domain and $\delta_{(f)}$ is a relative fluctuation of random frequency characteristic. The average value $\delta_{(f)}$ of the relative fluctuation of random frequency characteristics is 0. In this case, power spectrum of echo $S_{(f)}$ is given by the following equation (2):

$$S_{(f)} = S_0(f)|R(f)|^2 = S_0(f)|R_0(f)|^2(1+\delta_{(f)}) = \bar{S}_{(f)}(1+\delta_{(f)}) \quad (2)$$

Where, $$\bar{S}_{(f)} = S_0(f) \cdot R_0^2(f)$$

$\bar{S}_{(f)}$ includes attenuation in both a travelling and returning direction to and from the depth z where the domain exists. An average reflection characteristic of such domain and $\delta_{(f)}$ has information about the arrangement of random reflectors within the domain. For the measurement of characteristic values such as attenuation coefficient and average reflection coefficient, etc., the scallop factor $\delta_{(f)}$ becomes an error factor.

In order to eliminate adverse influence of $\delta_{(f)}$, a statistical average has been utilized. For this purpose, the power spectrums of k domains in the periphery, which are assumed to have the same property as the object domain, are obtained and the simple additional average is obtained from them. Thereby, diversion $V_{[\delta]}$ of average value of $1 + \delta_{(f)}$ is reduced to $1/k$ by average means of k power spectrums. However, this method requires about 100 domains as a value of k in order to obtain sufficient accuracy from the point of view of diagnosis when, for example, measuring a proportional constant for the frequency in the attenuation coefficient α (in a living body, it is known that $\alpha = \beta F$, β being the attenuation slope). The time window width (corresponding to $\Delta z$) must be substantially wider than the pulse length in order to correctly obtain the spectrum. That is, the time window width should be about 10 μs for a pulse length of about 1 μs and it can be converted to the length of domain of about 7.5 mm when the sound velocity is assumed as 1500 m/s. The diameter of an ultrasound beam is 3~5 mm in the frequency range used in diagnosis. Therefore, for example, when the k domains (m × n, where m domains on a single scanning line as the particular interest domains and n scanning lines) are selected for the ultrasound echo tomographic image, the domains are arranged into almost a square as a whole, where a square of about 5 cm × 5 cm can be obtained when $k \approx 100$, $m \approx 6 \sim 7$, $n \approx 15$. It has been a disadvantage in this method that selection of a wider domain within a single tissue is possible only in a large organ such as a liver. Moreover such selection cannot be adapted to a minute focal lesion such as tumor or initial stages of cancer, even in the liver, and it has been adapted only to diffusion lesion such as cirrhosis and fattiness.

Various attempts have been made to reduce the space required for measurement, namely by enhancing spatial resolution by suppressing as much as possible the random variable $\delta_{(f)}$ and reducing as much as possible the number of samples k required for a statistical average by a method other than the spacial statistic average. These attempts will then be explained hereunder.

The first method obtains a spectrum where spectrum scalloping is reduced by utilizing a homomorphic filter. By this method, a beta is obtained through various processings of the spectrum. Such a method is taught in U.S. Pat. No. 4,545,250 to Miwa, the same inventor as that of the subject application. In this method, a logarithmic value $\ln S_{(f)}$ (common logarithm or dB may be used) of power spectrum $S_{(f)}$ is obtained, is then Fourier-transformed into cepstrum, and the desired processings such, as application of a low-pass window, obtaining a moving average, and smoothing by median filter (described later) are carried out. The processed cepstrum is then reverse Fourier-transformed into the logarithmic power spectrum $\ln S_{p(f)}$, moreover, the power spectrum $S_{p(f)}$ is obtained after the processing and after obtaining the reverse logarithm, and the attenuation coefficient is obtained from such $S_{p(f)}$. In $S_{p(f)}$, $\delta_{(f)}$ is suppressed in comparison with $S_{(f)}$. Miwa '250 discloses the processing of the smoothing of the power spectrum on the cepstrum, not the processing on the logarithmic power spectrum. The smoothing of the power spectrum is processed directly in the present invention. Most of the processings disclosed in the prior art are linear processings, although some nonlinear processings are also included. Moreover, among the processing methods disclosed in the prior art, only the low-pass window processing is effective for the smoothing process on the cepstrum.

The second method fits a model spectrum to the raw spectrum $S_{(f)}$, obtained by the actual measurement of the spectrum, or logarithmic spectrum ln $S_{(f)}$ by formulating such model spectrum. For example, in such a model that the attenuation coefficient $\alpha = \beta f$, $\beta$ is constant between the depth $z_1$ and depth $z_2$, namely between $D = z_2 - z_1$ and dependency on frequency of reflection coefficient at the depths $z_1$, $z_2$ is equal. Accordingly, the (3) following relations can be obtained:

$$\ln S_{1(f)} - \ln S_{2(f)}$$
$$= 4\beta fD + \ln(1 + \delta_{1(f)}) - \ln(1 + \delta_{2(f)}) \qquad (3)$$
$$= 4\beta fD + h_\epsilon + \epsilon_{(f)} \qquad (3\text{-}1)$$

Where, $\delta_{1(f)}$ is a random variable of equation (1) at the depth $z_1$ and $\delta_{2(f)}$ is a similar random variable at the depth $z_2$. The left side of equation (3) is actually a measured value. The first item in the right side is the spectrum of frequency modeled to the linear function, and the second and third items on the right side of the equation are random variables which become the random variables $\epsilon_{(f)}$ in equation (3-1). The above method is discussed in R. Kuc et al "Estimating the Acoustic Attenuation Coefficient slope for liver from reflected ultrasound signals" IEEE, SU-26, No. 5, pp. 353-362, September 1979. As is well known, any linear function of a variable f can be expressed as pf+q, where p and q are coefficients defined for each linear function. In this case, the linear equation pf+q is curve-fitted to the plot as the frequency function of the actually measured value in the left side of equation (3) by the least mean square error method and a value $\beta$ is obtained from the slope p. This is called the spectrum difference method and is discussed in an article by R. Kuc entitled "Estimating acoustic attenuation from reflected ultrasound signals; comparison of spectral shift and spectral-differences approach, IEEE ASSP-32 No. 1, pp. 1-6, February 1984.

A Gaussian distribution is assumed for the send spectrum in addition to the modeling of linear attenuation coefficient $\alpha = \beta f$ for frequency, and dependency on frequency of reflection coefficients of $z_1, z_2$ is also assumed equal. Both $S_{1(f)}$ and $S_{2(f)}$ show the Gaussian distributions of the center frequencies of such spectrums becoming $f_{01}$, $f_{02}$, and the divergence of spectrum, namely the standard deviation $\sigma$ is equal in such spectrums. Moreover, there is a relation expressed by the following equation (4) between these two center frequencies. In addition, $\beta$ can be obtained from the equation (4) and this is called the center frequency transition method.

$$f_{01} - f_{02} = 4\sigma^2 \beta D \qquad (4)$$

$f_{01}$, $f_{02}$ can be determined respectively from the 0th moment and primary moment of the spectrums of $S_{1(f)}$. The $S_{2(f)}$ and the method of obtaining $\beta$ from $f_{01}$, $f_{02}$ thus obtained is called the moment method.

The logarithm of the equation (2) can be obtained from the following equation (5) and the item $(1 + \delta_{(f)})$ is not the multiplication item but becomes the addition item as indicated below.

$$\ln S_{(f)} = \ln \bar{S}_{(f)} + \ln(1 + \delta_{(f)}) = \ln \bar{S}_{(f)} + n_{(f)}$$
$$n_{(f)} = \ln(1 + \delta_{(f)}) \qquad (5)$$

ln (f), namely ln $(1 + \delta_{(f)})$ is a random variable, an average value becomes a constant value $h_n$ and n(f) becomes a random variable fluctuating around the average value. When $\bar{S}_{(f)}$ *is the Gaussian distribution*, *ln* $\bar{S}_{(f)}$ becomes a parabolic equation of f and the parabolic equation $pf^2 + qf + r$ can be curve-fitted to the actually measured value in the left side by the least mean square error method because $n_{(f)}$ becomes uniform additional random variables for the frequency. The center frequency $f_0$ of the Gaussian distribution and frequency standard deviation $\sigma$ can be obtained from these p and q.

$$2\sigma^2 = -1/p, f_0 = -q/2p \qquad (6)$$

A value of $\beta$ can be obtained by substituting $f_0$ of the equation (6) into the equation (4). This method is called the parabola application method R. Kuc "bounds on estimating the acoustic attenuation of small tissue regions from reflected ultrasound" IEE Proceedings to be published.

In the model of Gaussian spectrum and attenuation coefficient of frequency linearity, the frequency standard deviation $\sigma$ becomes a constant value as explained above. R. Kuc has announced the method that the parabolas $(-\frac{1}{2}\sigma^2)f^2 + (2f_0/2\sigma^2)f + r$, ($\sigma^2$: constant) having the constant coefficient of $f^2$, form various $f_0$. These are correlated with the left side of the equation (5) and a value of $\beta$ is obtained considering $f_0$ which makes maximum the correlated value as the center frequency. This method is called the correlation method or Matched-filter method.

Here, various methods described above are compared. In any of the spectrum difference method in the logarithm spectrum region, the parabola application method and the matched filter method, the model spectrum, not including random variables, is fitted to the spectrum, including random variables by linear processing.

The inventors of the present invention have investigated, by computer simulation, the influence on the value $\beta$ of the scallop by applying the spectrum difference method and parabola application method to the pseudo echo signal generated from the line of random reflectors. This confirmed that there is no particular difference between these methods.

R. Kuc has also investigated an error of value of $\beta$ caused by scalloping in the same way as above for the simple moment method where a value $\beta$ is extracted directly from the moment of the power spectrum of true value region, the matched filter (correlation) method, the Zero-Cross-Density method which is one of the time region processing and also made it obvious that the accuracy of the spectrum difference method and the matched filter method is more better than that of the other two methods and said two methods provide almost the same accuracy.

The inventors of the patent invention have attempted the technique by the inventors of smoothing the logarithmic spectrum by use of a moving average of adjacent spectral points and then adopting the spectral difference method or the parabolic method or its correlation-maximization variant to produce the local beta value. Regarding spatial/temporal resolution, the obtained results have little improvement over beta obtained from these methods using directly measured values and the aforementioned statistical averaging.

From the above explanation, it is obvious that the spectrum difference method, parabola application method and matched filter method on the logarithm spectrum are the best methods and these three methods give the same accuracy of the value of $\beta$. R. Kuc has indicated that the spatial average is still necessary when measuring with such best methods and the ultrasound apparatus for diagnosis which can be used practically has the limit of theoretical space resolution of 2 cm×2 cm.

However, as the diagnostic apparatus, such resolution of 2 cm×2 cm is still insufficient. For example, resolution of at least 1 cm×1 cm or less is necessary for judging that a tumor is malignant or benign. When a cancer of 1 cm or larger is found, it often has already spread to another part of the body. As explained above, the conventional method has a disadvantage that it gives insufficient space resolution. Moreover, a statistical average method takes a longer time for measurement and is inferior in practical use.

The present invention is intended to reduce and improve such disadvantages of the prior arts.

SUMMARY OF THE INVENTION

It is an object of the present invention to provide a medium characteristic measuring system which reduces an error of medium characteristic values by spectrum scallop and reduces a number of space average samples and improves space resolution by combining the model spectrum method with the parabola application method and including nonlinear processing medium characteristic values.

The present invention adopts a model spectrum obtained by modeling the medium characteristic to the measured power spectrum of the echo signal from the measured medium region, extracts medium characteristic values, and adopts the application processing including non-linear processings, thereby extracting characteristic values with a higher accuracy which exceeds the limit of adoption by linear processing, and reduces the required number of space average samples and measures space distribution of said characteristic value with high space resolution.

PREFERRED EMBODIMENTS OF THE INVENTION

The present invention is used to measure an ultrasound attenuation coefficient slope of a living tissue.

Figure 1A:
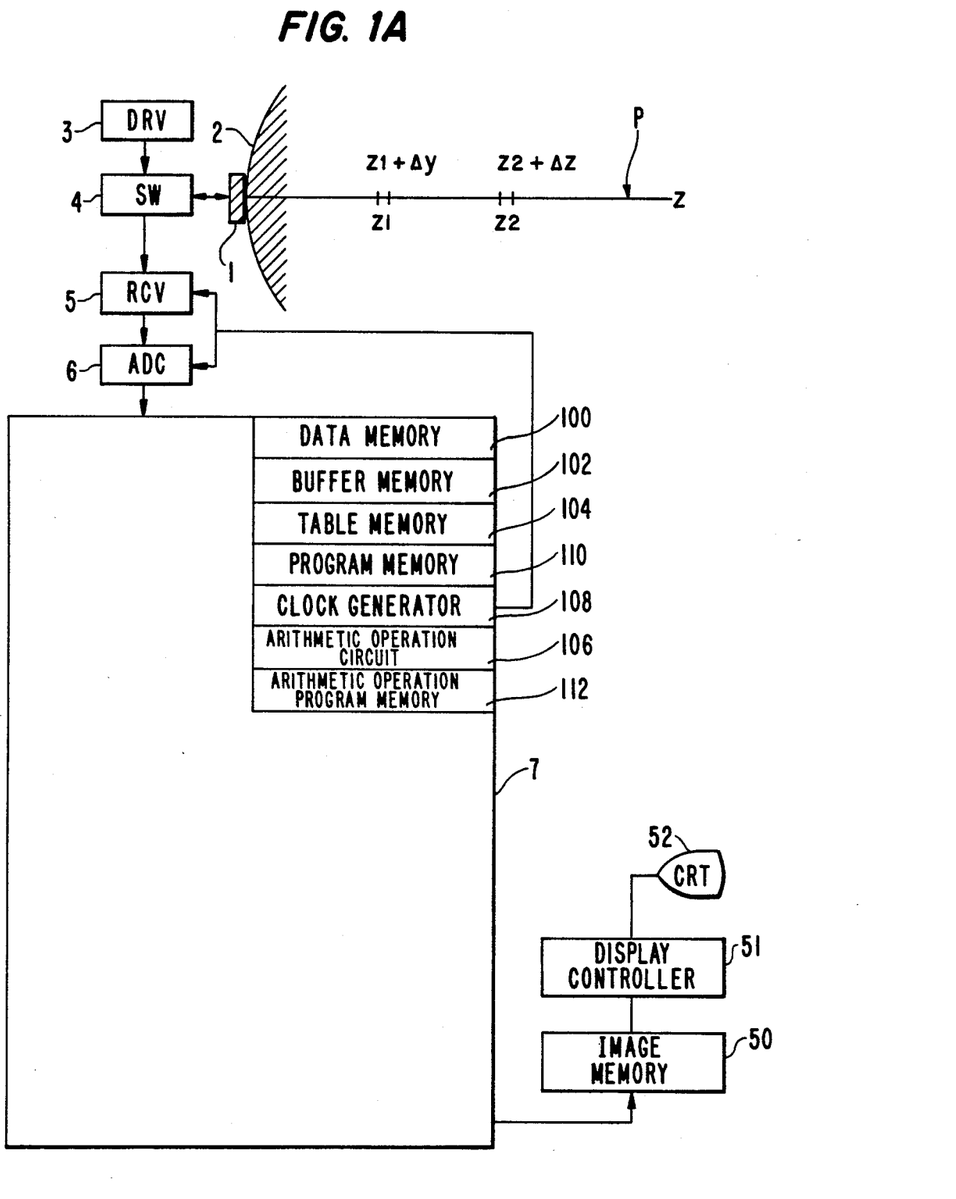
FIG. 1a is a block diagram of a measuring apparatus of the present invention.

FIG. 1a is a block diagram of an embodiment of the present invention. This embodiment uses, as the non-linear application processing, a means combining the moving window median filter (nonlinear processing) on the log power spectrum and the succeeding least mean square method (linear processing). As the model, the series 20-25 in FIG. 1b uses a desired spectrum shape as the send pulse and is based on the spectrum difference method. It is assumed as given that the attenuation coefficient $\alpha$ of tissue is expressed linearly with respect to the frequency by the equation $\alpha=\beta f$ ($\beta$ is a proportional constant) and that dependency on frequency of reflection coefficient is uniform for the tissue depth. In FIG. 1c, the series 30-3r5 is based on the parabola application method of center frequency transition method using the send pulse spectrum of the Gaussian distribution. Either one of the series 20-25 and 30-35 can be used. It is no longer required to use two systems simultaneously.

Numeral 1 denotes an ultrasound transducer which sends the ultrasound pulse P in the direction Z from the surface of medium 2, using a driver 3. The transmitted pulse travels in the direction Z within a living body. The reflected waves are generated from living body tissues at various points. The reflected wave runs in a direction opposite to direction Z. The echoes from shallower regions return most quickly to the transducer 1 while the echos from the deepest region returns more slowly to the transducer 1. These reflected echoes are all received by the transducer 1. Since reflectors exist closely and almost continuously in the medium, the received signals become a continuous signal with the pulse send time considered as the time origin (t=0). The reflected echoes corresponding to the depths $z_1 \sim z_1+\Delta z$ are reflected signals between the times $t_1=(2z_1/c)\sim(2z_1/C+T)$. (Note: T 2z/c; C=sound velocity), 4 is a switching circuit which switches the signal path for sending and reception. 5 is an amplifier for receiving signal. 6 is an A/D converter which converts the amplified received analog signal to a digital signal and sends it to a control and operation unit 7. This control and operation unit 7 can be formed easily with a microcomputer, for example. This unit includes a data memory 100, a buffer memory 102, a table memory 104, an arithmetic operation circuit 106, a clock generator 108, a control program memory 110 and an arithmetic operation program memory 112. These memories may be replaced with the memory regions assigned to a single memory. 8-11, 20-25 (or 30-35) are outlines of flowcharts of arithmetic operation processing programs. The output data of AD converter 6, concerning a single pulse sending and receiving cycle, are stored in the data memory. Step 8 is the time window gate processing. A train of data between the time t (corresponding to the interest depth z) and the time t+T (corresponding to z+Δz) is extracted from the memory and is stored in the buffer memory. 9 is the discrete Fourier transform processing which can be done completely with software. The discrete Fourier transform processing can also be done with hardware connected with a microcomputer in order to curtail the processing time. A train of data extracted with the time window in the buffer memory is Fourier-transformed and thereby the power spectrum as a function of frequency can be obtained. 10 is the step for converting the spectrum into the logarithm, wherein the power spectrum is converted to the logarithm power spectrum using the true value-logarithm conversion table which has been stored in the table memory. 11 is a compensation step where a so-called geometrical factor is carried out. Step 11 is for compensating the distortion of a spectrum due to nonuniformity of a three dimensional diffraction effect of a beam. The beam corresponds to the depth (in the travelling direction) of an ultrasound beam and Gaussian compensation when the actual spectrum is a non-Gaussian distribution, in such a case that the Gaussian distribution spectrum is necessary as in the case of the 30–35 series. The compensating coefficients are given as the function of frequency for the depth and these can previously be obtained by actual measurement (in the non-attenuation medium). Such compensating coefficient is previously stored in the table memory and compensation is carried out by reading the compensating coefficient corresponding to the depth z. See Miwa, U.S. Pat. No. 4,509,528 and H. Miwa et al. "Reduction from 3 dimensions to 1 dimension in quantitative measure of reflection, using G-factor" Jour. of Ultrasound in Medicine, vol. 3 No. 9, p. 226, September, 1984.

Figure 1B:
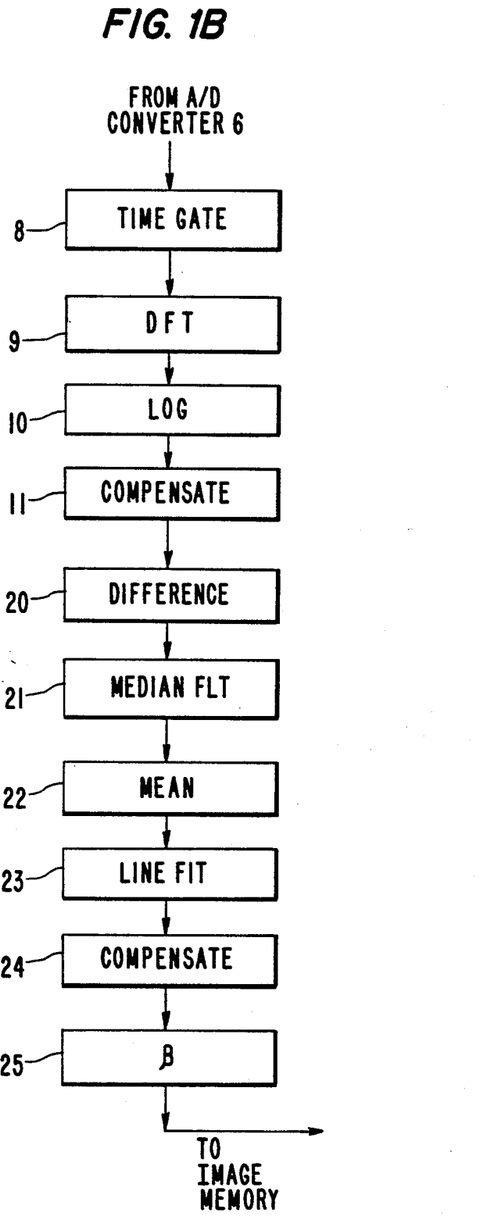
FIGS. 1b and 1c are flow charts showing the processing steps of the present invention.
Figure 1C:
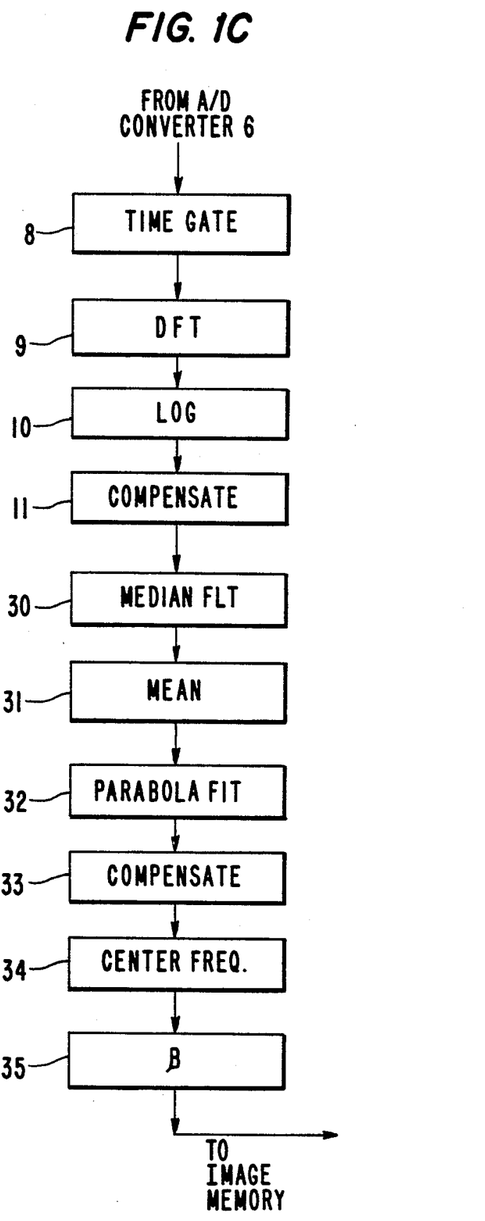
Figure 2A:
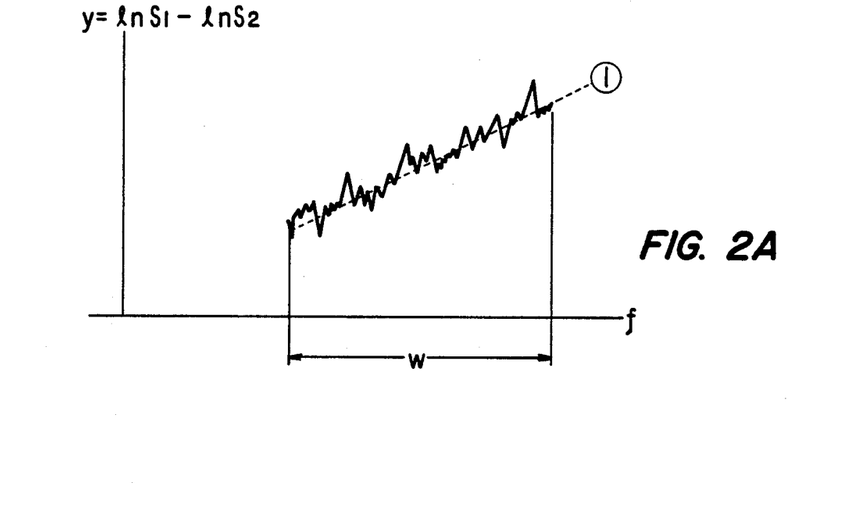
FIGS. 2a and 2b are graphs showing the spectrum difference method.
Figure 2B:
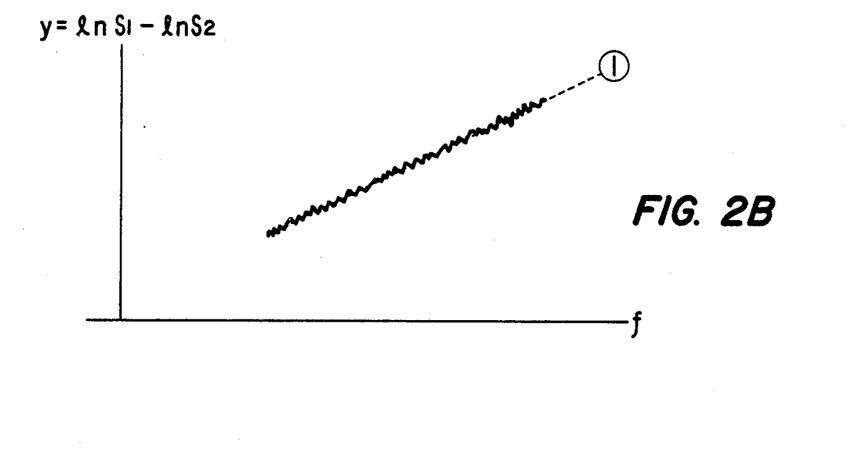

The flow of signal processing is explained for steps 20–25 in FIG. 1b. Step 20 is the subtraction (linear processing) between the compensated log power spectrum ln $S_{1(f)}$ corresponding to depth $z_1$ (which is an output of 11) and ln $S_{2(f)}$ corresponding to depth $z_2$ (which is deeper by the distance D). This operation corresponds to the equations (3) and (3-1) explained above. This actually measured value, namely the left side of the equation (31), can be indicated as shown in FIG. 2A. This spectrum changes at random almost around the straight line ① in the effective signal band W of the sending and receiving system. Conventionally, the model spectrum $pf+q$ is curve fitted in the range of W to the spectrum of FIG. 2A with the Least Mean Square Error Method (LMSE method). A value of $\beta$ has been obtained from the relation of $\beta = p/4D$. However, $\beta$ is influenced by the random variable $\epsilon_{(f)}$ and therefore an accurate measurement of $\beta$ cannot be obtained. This is because the data of FIG. 2A does not include a sufficient number of samples mutually independent of each other. Usually, the time gate width T is set to about 10 μs. In this case, frequency resolution $\Delta f(1/T)$ becomes 0.1 MHz. Since W is determined as about 2 MHz in the current technique, a number of independent samples (fi) is equal to about $W/\Delta f=20$. Therefore, the probability that the average of 20 $\epsilon_{(f)}$ becomes zero is not sufficiently high, the frequency distribution is not symmetrical for positive and negative values and the frequency distributions in the respective sections W/2 in the right and left sides of W are not equal. Thus, an error is introduced into p. It is possible to increase the number of samples only in the spatial average, and the spatial average degrades the space resolution. The series 20–25 of this embodiment executes the moving window median filter processing (step 21) which is nonlinear processing and applies the model spectrum $pf+q$ with the LMSE method (step 23) after smoothing, as shown in FIG. 2B. The median filter eliminates the excessively separated sampling points and recovers positive and negative symmetry of the frequency distribution of $\epsilon_{(f)}$, and also reduces the diffraction effect. Particularly in the LMSE method, the excessively separated sampling points has a large influence on p but the median filter eliminates such excessively deviated sampling points and increases the accuracy of p. Therefore, a number of space averages (step 22) k can be reduced and space resolution can be increased.

Figure 5:
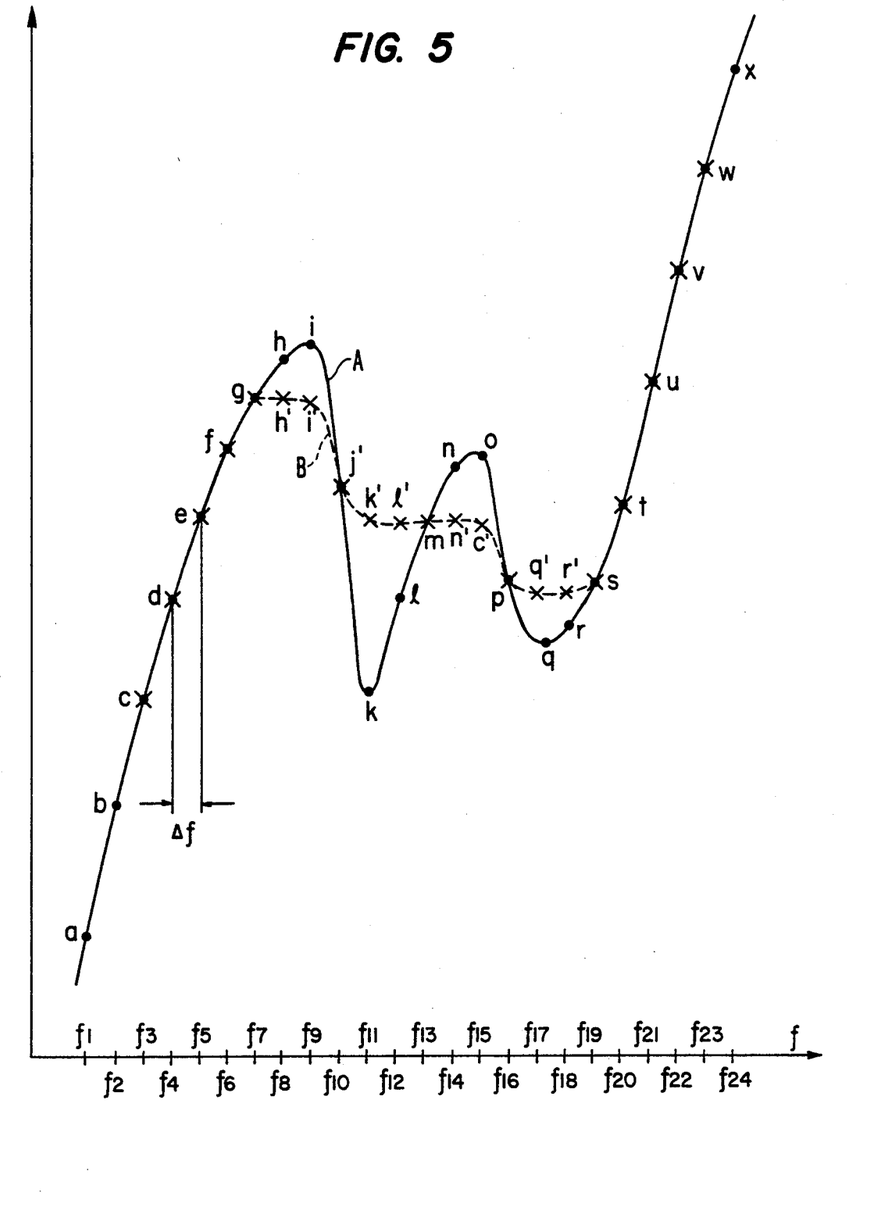
FIG. 5 is a graph of median filter processing.

FIG. 5 is graph of median filter processing. In this figure, frequency is plotted on the horizontal axis, and measured values of the waveform A, sampled in every constant frequency, plotted on the vertical axis. In median filter processing, the processing wherein the center value of odd number of continuous sampled values arranged sequentially from larger side is considered as the sampling value at the center frequency. For example, in a case where five sampling values a–e are considered, the center value of those arranged sequentially from the larger side, namely the third value, is equal to the value of C. This value is employed as the sampling value at the central sampling point $f_3$ of five sampling frequencies. Therefore, when the waveform increases or decreases monotonously, the result does not change even when the filter processing is carried out.

However, in the case of the median processing, for example, at the sampling point $f_8$ shown in the figure, the sampling values f–j can be arranged sequentially from the larger side as (i, h, g, f, j). Since the center value is g, this value becomes the value h' after the filter processing at the point $f_8$. In the case of the median filter processing at the point $f_9$, the sampling values g–k can be arranged, in the same way, as (i, h, g, j, k). The center value is g. Therefore, the sampling value at $f_9$ also becomes i' which is equal to the value for g. The values of median processings are indicated as X, in the same way and the waveform B of the dotted line can be obtained by connecting such values X. As is obvious from the figure, the peak value is suppressed and waveform is smoothed.

The more the sampled values exist for the reference at a time, the more distinctively suppression occurs. A degree of suppression can be obtained in accordance with experiment or simulation.

In practice, the median filter processing may be done directly for the data point group of FIG. 2A. Namely, it also possible that as the substep 1, the LMSE method is adopted in order to obtain $p'f+q'$. As the substep 2, such value is subtracted from each point in FIG. 2A. The median filter processing is executed to such difference as the substep 3 and $p'f+q'$ is added as the substep 4.

The space average 22 is a linear processing and it may be inserted at any position in all steps. However, in case all steps are divided with the nonlinear processing, there is no difference in the result even when such linear processing is inserted to any position within the same section. But if the section changes, however, a difference appears in the accuracy and therefore the optimum inserting section should be determined by experiment. In the same section an, inserting position is generally determined so that the total amount of calculation is minimized and the processing time becomes shortest.

24 is the nonlinear application distortion compensating step. The filter 21 suppresses the random variables $\epsilon_{(f)}$ in the right side of the equation (3-1). and simultaneously may deviate the model spectrum of the first item of the right side of the equation (3-1). In case the model spectrum is linear, the median filter processing does not generate any distortion in (21-1) and (21-2) described above and the compensating step can be omitted. But it is indicated because of general description. An example of distortion is explained in the series 30–35.

Figure 3A:
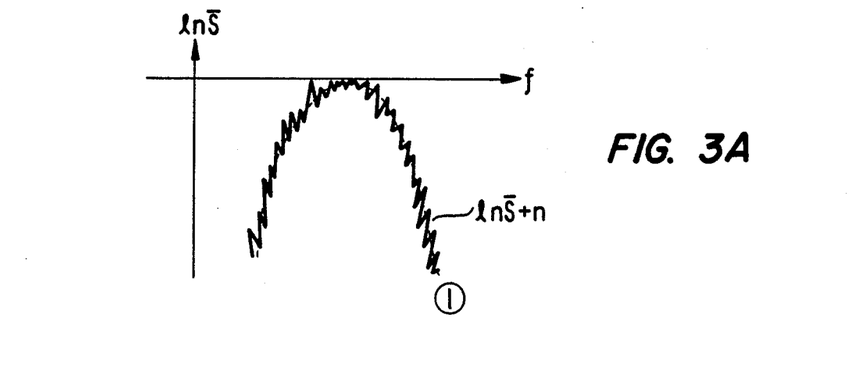
FIGS. 3a-3c are graphs showing the parabola application method.
Figure 3B:
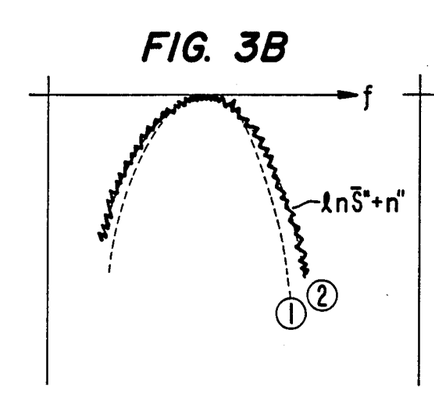
Figure 3C:
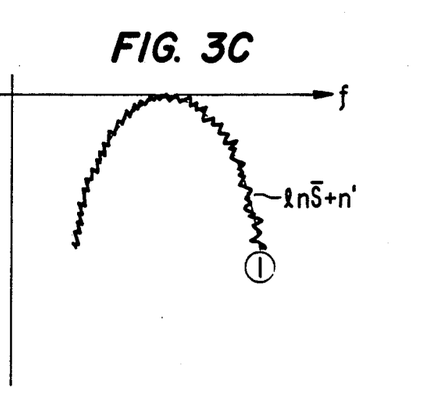

An example where the series 30–35, shown in FIG. 1c is used is explained hereunder. In this case, the Gaussian distribution type ($\sigma^2$ is known) send pulse spectrum is used and a value of $\beta$ is obtained from the center frequency transition of the equation (4) and the parabola adoption method is used for measurement of center frequency. The median filter processing of step 30 is immediately carried out for the compensated logarithm power spectrum which is an output of 11. As shown in FIG. 3A, in the output of 11, the random variables $n_{(f)}$ are superposed on the parabola ln $\bar{S}_{(f)}$ (① in the figure). The step 30 is capable of employing the method for direct processing as in the case of series 20–25. The method where $p'f^2+q'f+r'$ is obtained first by adopting LMSE as the step (30-2), then $p'f^2+q'f+r'$ is subtracted from each point of FIG. 3A, the median filter processing is executed to the result of such subtraction and then $p'f^2+q'f+r'$ is added again. In the step (30-2), since the median filter executes processing after removing the parabola component from FIG. 3A, the model spectrum receives little distortion. Accordingly, the suppressed random variables $n'_{(f)}$ is superposed on the parabola ln S(① in the figure) which is the model spectrum as shown in FIG. 3C. In the step (30-1), the median filter processing is executed while the parabola component of FIG. 3A is included and therefore the model spectrum receives partial distortion and thereby the random variables $n''_{(f)}$ which are slightly suppressed, are superposed on the distorted parabola ln $\bar{S}''$ as shown in FIG. 3B ②. ln $\bar{S}''0$ is equal to that obtained by executing the median filter processing to ln $\bar{S}$. The peak region is suppressed. Then the peak region is normalized again to the same level again, the width looks to be widened.

Therefore, the nonlinear applicable distortion compensation processing in the step 33 can be omitted for the step (30-2) but is required for the step (30-1). As shown in ② of FIG. 3B, the maximum value position (center frequency) of the parabola does not receive distortion but the diffraction effect of the parabola (corresponding to $\sigma$ in Gaussian spectrum) is wide-spread. In FIG. 3B, the distortion-free model spectrum ① is also indicated by a dotted line. Therefore, in the case of step (30-1), the filter distortion compensation in the step 33 is unnecessary when focusing only on the center frequency as the parameter of model spectrum, but compensation is also necessary it is required to extract the divergence $\sigma^2$ of Gaussian distribution from the model spectrum as another parameter considering a model spectrum of a higher order.

An example of a compensating method for distortion of a model spectrum in such a case as requiring such divergence $\sigma$ is explained below. In the first example, the processings of step (30-1) are executed prior to application of various parabolas $yj=p_jf^2+q_jf+r_j$ (ideal parabolas having no partial distortion by $\epsilon_{(f)}$) in order to obtain $y_{j(f)}$ distorted by the median processing $y_j$ corresponding to the pairs $p_j$, $q_j$ is obtained, application is made by $y_j$ in place of $y_j$ in the step 32, and $p_j$, $q_j$ corresponding to the $y_j$ of optimum application are obtained from the previously obtained correspondence. In the second example, the distortion index of distortion model spectrum of ② of FIG. 3B is specified, and correspondence between such distortion index and $p_i$, $q_i$ is previously obtained for various $y_j$. In ② of FIG. 3B, the center frequency does not change and only the diffraction effect changes. Therefore, only one distortion index corresponds to all $y_j$. For example, as the distortion index, the model spectrum curve $y_j$ 11 2 of FIG. 3B is extracted in the range from the maximum value to, for example, a value of 40 dB or less, a ratio $v_j$ of second order moment and 0th order moment around the center frequency is obtained for the shape and it can be used as the distortion index. Since a correspondence of 1:1 exists between $v_j$ and $p_j$, $q_j$, $v_j$ is obtained from an output of 30 and $p_j$, $q_j$ can also be obtained therefrom. The third example is a more simplified method. From the application under the assumption that $y_j$ is also parabola, $y_j=p_jf^2+q_jf+r_j$ can be obtained and when the relation between $p_j$, $q_j$ and $p_j$, $q_j$ for $y_j$ to which the processing of 30 is executed to various $y_j$ is obtained previously, $p_j$, $q_j$ can be obtained from correspondence considering the output p, q of 32 as $p_j$, $q_j$.

From $p_j$, $q_j$ thus obtained, the center frequency $f_0$ and divergence $\sigma^2$ of spectrum can be obtained by the equation (6). This is the step 34. In the step 35, $\beta$ is further obtained by the equation (4).

The step 31 is a spatial average and the explanation for 22 series 20 is directly adopted.

As explained above, a value of between the depths $z_1$ and $z_2$ can be obtained and distribution of $\beta$ can also be detected for all depths in the same way. The setting of $D=\Delta z$ is generally made for obtaining fine distribution of $\beta$. Moreover, distribution of $\beta$ is obtained as the function of z for other scanning lines and bidimensional distribution of $\beta$ on the particular section can be obtained by repeating this process. The data bus obtained are stored in the image memory 50. 51 is a display controller which reads the contents of the image memory so, for example, in the sequence of raster scanning of television and displays distribution of $\beta$ on the CRT 52 with brightness or pseudo colors.

The linear processing, such as the depth direction difference in the step 20, space average in the step 22 (or 31), average processing by moving window on the frequency axis and low-pass-filter processing, can be inserted between the step 10 and step 21 (or 30).

It is of course possible that an output of step 30 or 31 is converted to a true value from a logarithm, the moment of each order of Gaussian distribution spectrum is obtained, an average frequency and divergence of it are also obtained and the attenuation slope can be obtained by respectively approximating them as the center frequency and the divergence around it.

The difference between the step 11 and the model spectrum after compensating filter distortion yields $n_{(f)}-\bar{n}_{(f)}$ of equation (5). From the equation (5), $$n_{(f)}=\ln(1+\delta_{(f)})$$

hn: constant, $hn=\overline{\ln(1+\delta_{(f)})}=$constant

From equation (1), $$n_{(f)}=\ln(|R_{(f)}|^2/R_0^2).$$

Namely, data of scalloped power spectrum $|R(f)|^2$ can be obtained from $n_{(f)}$ and, moreover, a histogram of the interval of reflectors in the medium, a self-correlation function of reflector intensity distribution, the existence or not existence of quasi-periodic structure and medium characteristic values of such period, etc. can be obtained for the use in the diagnostic process.

Figure 6:
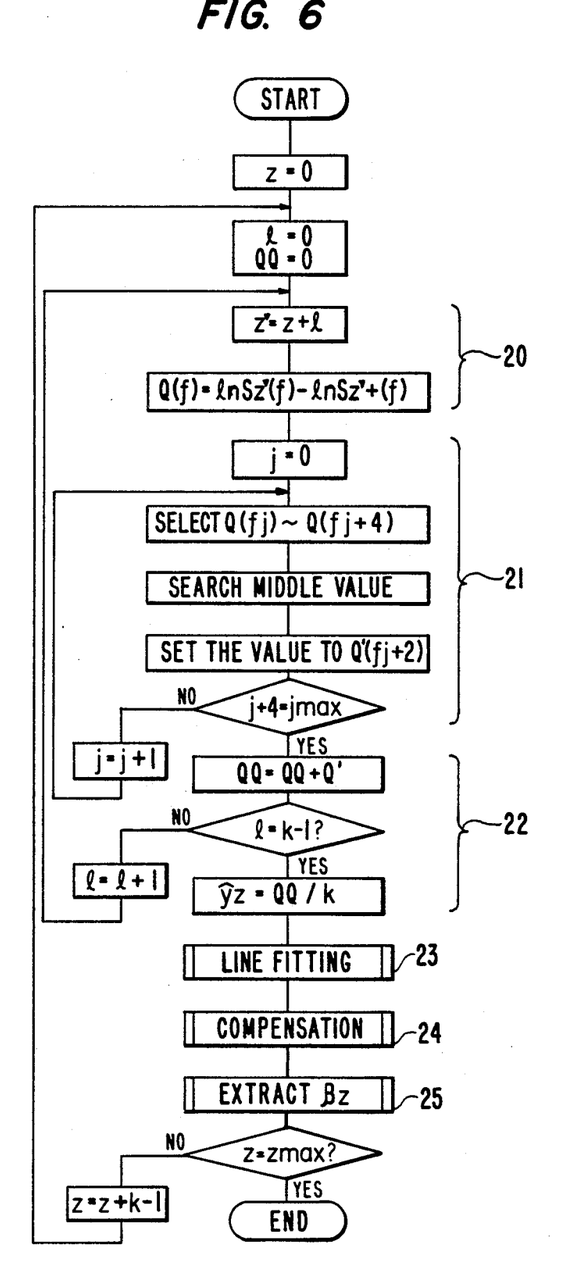
FIG. 6 is a flowchart of the processing of FIG. 1.

The flowchart of FIG. 6, which indicates in detail the steps 20-25 of FIG. 1 is explained below.

The log power spectrums at respective depths $z(z=0-Z_{max}-)$ are stored in the data memory by the steps 8-11 in FIG. 1.

Moreover, as the log power spectrums, the spectrum values at each frequency $f_j(j=0-j_{max}-)$ are also stored.

First, z, l, QQ are all zeroed. Here, l means the order (sequence) of k sampling points for obtaining space average in the depth direction and $l_{max}$ should be considered as $k-1$. QQ is a buffer region or content of it for accummulating k sample values to obtain the average value. $z+1$ is set as $z'$, data of log power spectrums at the depth $z'$ and $z'+1$ are read from the data memory, difference of such data is calculated for each frequency Fj. This value is then stored in the buffer region Q(f). This Q(f) corresponds to the waveform of FIG. 2A.

Here, five data of $f_j-f_{j+4}-$ are extracted from Q(f) under the condition of $j=0$, the center value among such five data is extracted and it is then stored at the position $f_{j+2}$ in the other buffer region Q'(f). One (1) is added to the value of J and the similar processing is repeated until $j_{+4}$ reaches $j_{max}$. This processing corresponds to the median filter processing explained in FIG. 5 and a difference spectrum after the filtering can be obtained at the buffer region Q'(f).

Since the capacity covering $f_{j+2}-f_{jmax-2}-$ is sufficient as the capacity of buffer region Q'(f), the amount of data can be reduced by four from that of buffer region Q(f).

When the median processing is completed for the depth $z'$, namely when $j+4$ becomes $j_{max}$, the content of Q' is (A) accumulated (ion) to the content of QQ (for each frequency. (A) accumulated (ion) of k data can be obtained at QQ by repeating (A) accumulated (ion) of k data for k depths $z'$ ($z-z+k-1$). The difference spectrum $y_z^-$ of space average for depth z can be obtained by dividing such QQ with k.

A slope can be obtained by said linear application for $y_z^-$, distortion is compensated as required and a value of $\beta_z$ can be obtained from such slope. Since the processing itself of linear application is known, explanation is omitted here.

Next, z is added by $+(k-1)$, and QQ are zero cleared and the same processing is repeated from the beginning. Thereby, depth $z=0$, $k-1$, $2k-1$, $3k-1$, . . . can be obtained sequentially. Here, z is caused to advance in the step k because it is necessary to give independence between k averages on the occasion of obtaining average value of k data. If there is a margin in the processing time of computer, it is also possible to obtain the average value between partly overlapping k data by causing z to advance in the step of k/2 or k/3. In this case, display of image becomes very smooth. However, in any case, the space resolution is certainly reduced to 1/k.

In the above explanation, an average value is obtained from k samples of the data on the same z axis. Actually, however, it is recommended that the k/r samples be obtained for each of the adjacent r scanning lines and the average value of such k values is obtained. Since it is easy to modify the program of FIG. 6 for this purpose, further explanation is omitted here. Processings in the steps 30-35 in FIG. 1 are similar to those explained above and these are not explained here.

The present invention can be used, as explained above, in executing nonlinear filter processing to a power spectrum but, it is not intended to be used solely for smoothing of spectrum waveform. Sufficient effect cannot be obtained for improvement in accuracy of $\beta$ even through the smoothing process with an existing linear filter, for example, a low-pass-filter, etc. From the other point of view, the nonlinear filter maintains the original waveform under a certain condition and rejects the original waveform outside the certain condition. It is obvious from the result of simulation that improvement in accuracy of $\beta$ can be realized with such nonlinear filter. The reason for the improved accuracy is not yet clear but it is assumed that the extreme changing in the area of the spectrum does not correctly reflect the property of the medium. The nonlinear filter processing which suppresses such area can improve the overall S/N ratio. In operation of least mean square error at the application of model spectrum, the peak area of spectrum largely influences a total sum of the least mean square error and fluctuation can be reduced by eliminating such area.

Results of computer simulation are indicated below.

In the simulation, a first reflector train having random reflection coefficients are formed at random intervals utilizing a random number sequence. It is assumed that the attenuation slope $\beta$ is set, for example, to 1 dB/MHz/cm and ultrasound having a certain waveform is applied to such reflector train from the one direction. Therefore, the reflected waveforms can be obtained from such reflector train and such waveforms are combined in order to obtain the received echo signal. A value of $\beta$ is obtained from such an echo signal with the method explained above. Then a search is performed to determine how many errors such value has for 1 dB/MHz/cm. The method of steps 20-25 shown in FIG. 1 is employed for obtaining a value of $\beta$.

Figure 7A:
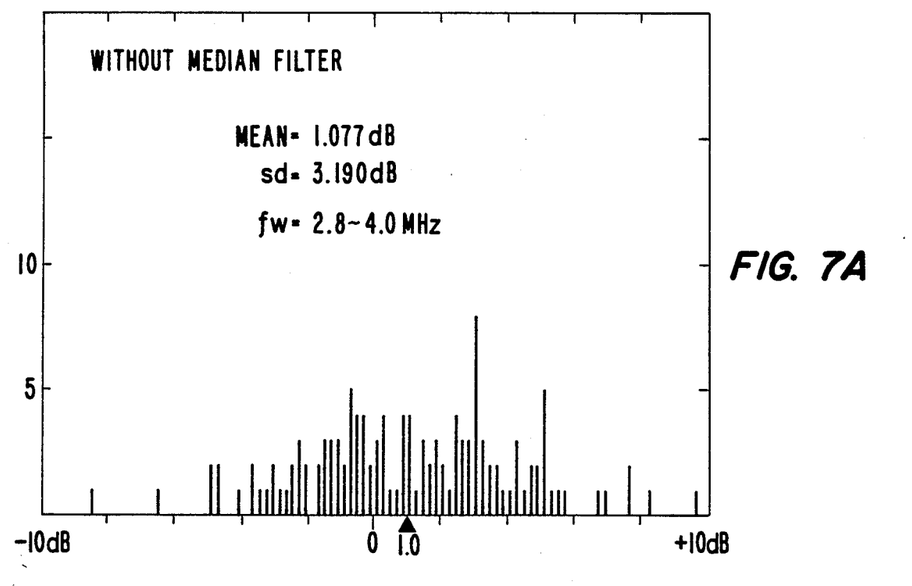
FIGS. 7a, 7b and FIGS. 8a and 8b are graphs of results of computer simulation indicating the result of the present invention.
Figure 7B:
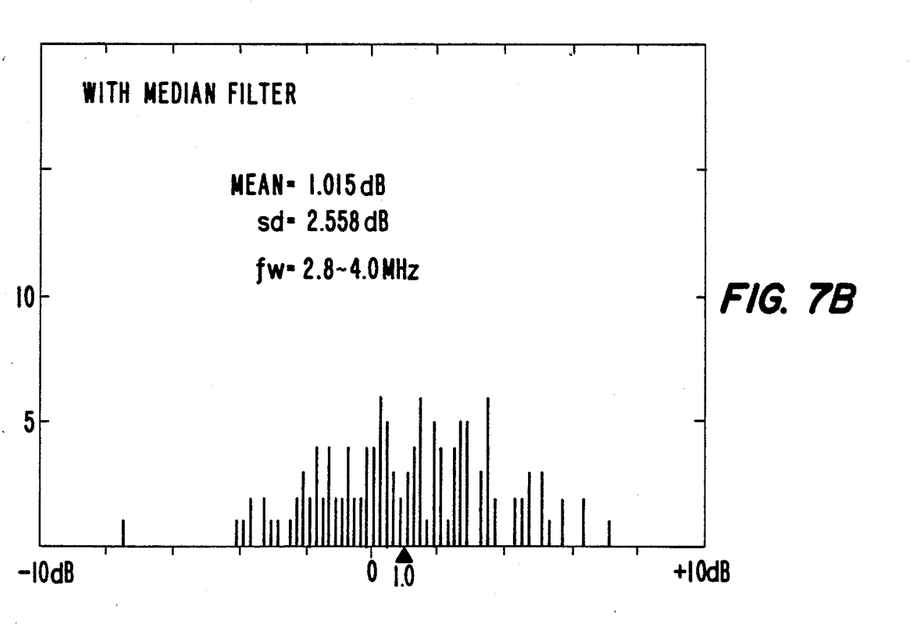

Such simulation is carried out to all of the 128 different random reflector trains (where $\beta$ is 1 dB/MHz/cm) both in cases where the median filter is effectuated and where it is not. FIG. 7 shows the obtained histogram of $\beta$. In FIG. 7A, the median filter is not effectuated, while in FIG. 7B, the median filter is effectuated. The vertical axis indicates a number of times of measurement, namely how many times the value $\beta$ appears among 128 trials, while the horizontal axis indicates measured values of $\beta$. A value given the mark "mean=" is an average of 128 measured values. Intrinsically, a value of $\beta$ should become 1.00. A value given the mark "Sd=" means the standard deviated value which indicates fluctuation of measured values. Smaller Sd value indicates lesser fluctuation. Therefore, it means that accuracy can be maintained even when an average sample number is reduced. $f_w$ is a bandwidth applied for the linear application operation.

Comparison between FIG. 7A and FIG. 7B proves that the mean value of FIG. 7B where the median filter is effectuated comes nearer to 1.0 and fluctation Sd is also smaller.

Figure 8A:
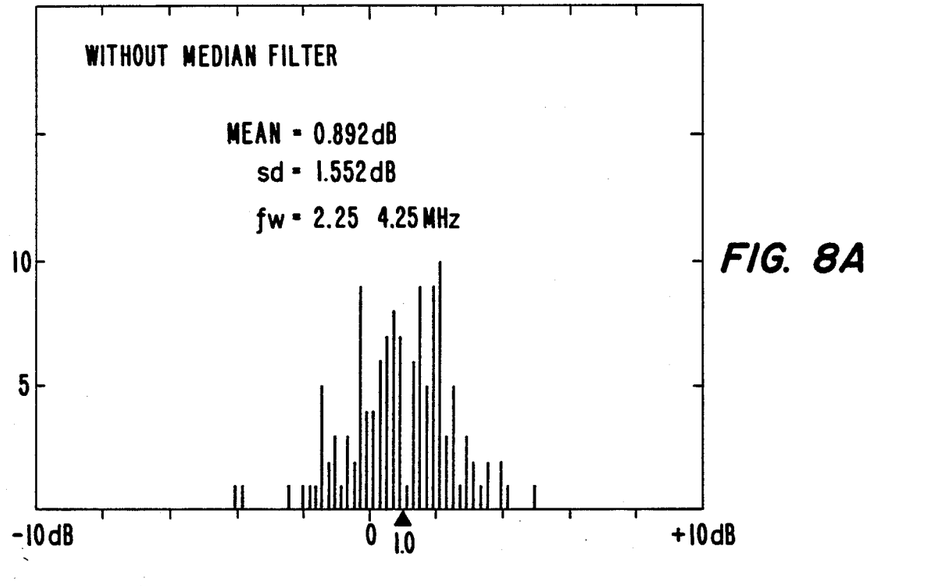
Figure 8B:
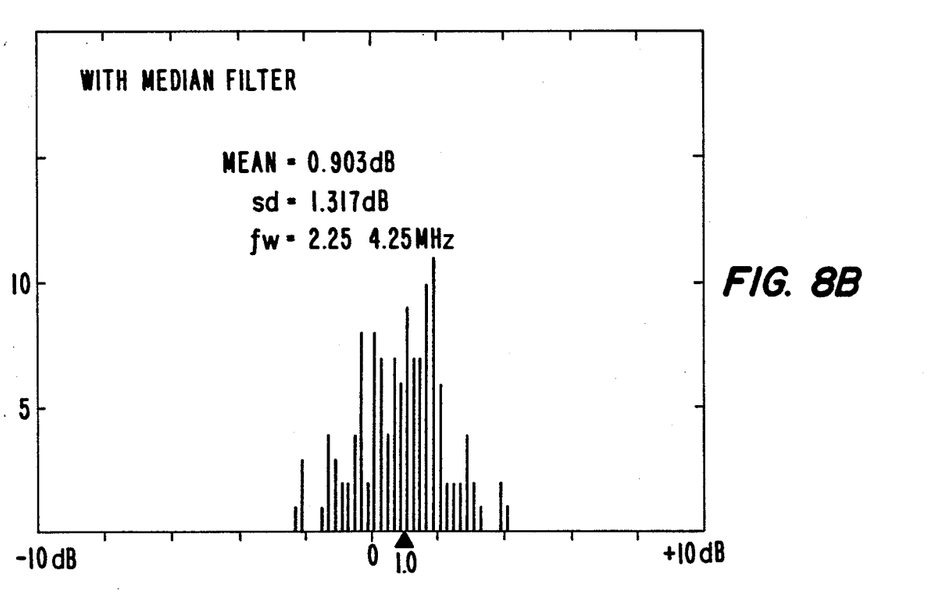

FIG. 8 shows the result of simulation where the bandwidth $f_2$ is widened and fluctuation $S_d$ is considerably smaller than that in FIG. 7. As in the case of FIG. 7, the mean is more nearer to 1.0 and fluctuation Sd is smaller in FIG. 8B than those in FIG. 8A where the median filter is effectuated.

As explained above, fluctuation Sd is reduced by about 20% by the present invention. If the same fluctuation is allowed, a number of samples to be averaged can also be reduced by about 40% and the spatial resolution can be improved as much.

Other Filtering Process:

The nonlinear filter of the present invention can be adopted to a means other than the median filter, if it holds the original waveform at the area where changes are gradual and suppresses only the sharp changing region.

Figure 4A:
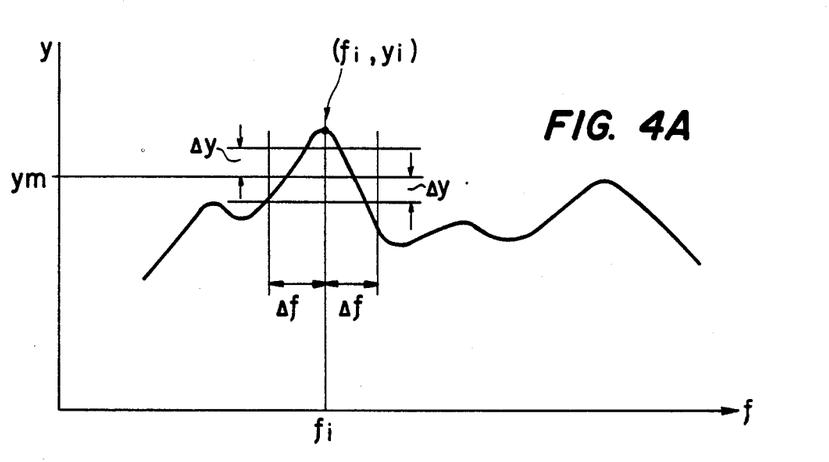
FIGS. 4a-4b are graphs of nonlinear filter processing.

FIG. 4A shows the filtering process for eliminating excessive deviation data points. This filter focuses a certain point $(f_i, y_i)$, obtains an average $y_m$ of y in the range of $\pm \Delta f$, and clips $y_i$ to $y_m + \Delta y$ when $y_i$ is separated by specified deviation $\pm \Delta y$ for $y_m$ or does not use the point $(f_i, y_i)$ to the successive application method.

Figure 4B:
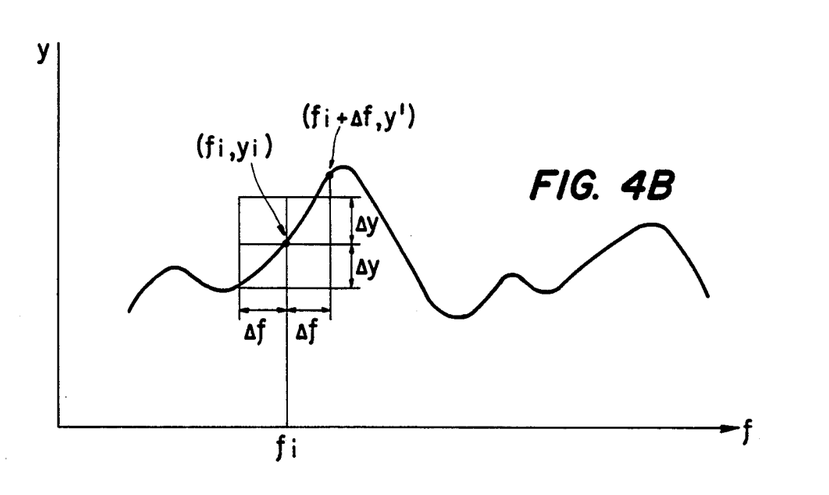

FIG. 4B explains the processing of a reverse hystresis filter. This filter focuses a certain point $(f_i, y_i)$ and clips value of y' of the point $(f_i + \Delta f, y')$ separated by $\Delta f$ from such point to $y + \Delta y$ when y' is larger than $y + \Delta y$ or does not use such point $(f_i + \Delta f, y')$ for the successive application processing.

In addition, the present invention can be adopted to such a filtering process where the sample points which show changes within the threshold level and the sample points which show changes larger than those mentioned above are clipped to a value within the threshold level, or such sample values are eliminated from the object of the successive processings.

We claim:

1. An ultrasound medium characteristic measuring apparatus which sends ultrasound waves into a medium and measures acoustic characteristic values of the medium by analyzing waves reflected from the medium, said apparatus comprising:

means for generating a plurality of ultrasound waves and for imparting these waves to the medium;

means for receiving ultrasound waves reflected from the medium;

gate means for extracting a reflected wave reflected from a particular depth of the medium from among the waves reflected from the medium, and for converting said reflected wave into a signal corresponding to said reflected wave;

means for obtaining a frequency spectrum based on said extracted reflected wave, means for performing nonlinear clipping filtering directly on said frequency spectrum and for providing a filtered spectrum, means for applying a model spectrum for modeling acoustic characteristic values of the medium to the filtered spectrum, and means for extracting the acoustic characteristic values of the medium from said application of the model spectrum to the filtered spectrum.

2. An ultrasound medium characteristic measuring apparatus according to claim 1, wherein said means for obtaining a frequency spectrum includes Fourier transform means for Fourier-transforming the reflected signal corresponding to the reflected wave from a particular depth, and for obtaining a log power spectrum from the logarithm of the transformed signal, and said model spectrum application means additionally for executing application processing using a parabola as the model spectrum.

3. An ultrasound medium characteristic measuring apparatus according to claim 1, wherein said means for obtaining a spectrum obtains respective log power spectrums from the reflected signals at two adjacent depths and additionally for executing a different spectrum from said reflected signals, and said model spectrum application means is additionally for executing the application processing using a straight line as the model spectrum.

4. An ultrasound medium characteristic measuring apparatus according to claim 1, 2 or 3, wherein said acoustic characteristic value extracting means includes means for obtaining an attenuation slope $\beta$ which is a proportional constant relating measured frequency to an attenuation coefficient of ultrasound in the medium.

5. An ultrasound medium characteristic measuring apparatus according to claim 4, wherein said means for performing nonlinear filtering is a median filter.

6. An ultrasound medium characteristic measuring apparatus according to claim 1, further comprising means for obtaining a mean value of outputs of said nonlinear filter means related to the reflected signals from adjacent plural depths provided between said means for performing nonlinear filtering and said model spectrum application means, whereof the model spectrum is applied to outputs of said means for obtaining such mean value.

7. An ultrasound medium characteristic measuring apparatus according to claim 1, wherein said nonlinear filtering process means comprises:

means for preliminarily fitting the model spectrum to a measured spectrum, means for obtaining a deviated spectrum between the measured spectrum and said preliminarily applied model spectrum, means for executing a nonlinear filtering process on said deviated spectrum, and means for adding said deviated spectrum, obtained by said nonlinear filtering process execution means, to the preliminarily applied model spectrum.

* * * * *

UNITED STATES PATENT AND TRADEMARK OFFICE
CERTIFICATE OF CORRECTION

PATENT NO. : 4,723,553

DATED : February 9, 1988

INVENTOR(S) : Miwa et al.

It is certified that error appears in the above-identified patent and that said Letters Patent is hereby corrected as shown below: Title Page:

Page 1, [57], line 12, "one" should be --are--.

Col. 1, line 50, after "discussed" insert --in H. Miwa et al, "Removing spectrum scalloping and frequency--;

line 60, $\bar{\delta}(f)$ should be --$\delta(f)$--;
line 62, $\delta(f)$ should be --$\bar{\delta}(f)$--.

Col. 2, line 25, $\beta F$" should be --$\beta f$--.

Col. 3, line 23, "(3) following relations" should be --following relation (3)--.

Col. 4, line 14, after "$\delta(f)$" insert --)--.

Col. 6, line 45, change "2z/c" to --2 $\Delta$ z/C--.

Col. 7, line 26, change "4,509,528" to --4,509,524--.

Col. 9, line 35, delete "0";
line 64, change "y$\hat{j}$" to --y$j$--; (2nd occurrence)
line 65, change "yj" to --y$\hat{j}$--.

UNITED STATES PATENT AND TRADEMARK OFFICE
CERTIFICATE OF CORRECTION

PATENT NO. : 4,723,553

DATED : February 9, 1988

INVENTOR(S) : Miwa et al.

It is certified that error appears in the above-identified patent and that said Letters Patent is hereby corrected as shown below:

Col. 10, line 2, change "yj" to --$\hat{y}j$--.

Col. 11, line 6, after "Zmax" delete "-";

line 9, after "jmax" delete "-";

line 18, "Fj" should be --fj--;

line 20, after "+4" delete "-";

line 29, after "fjmax-2" delete "-";

lines 35 and 37, change "(A) accumulated (ion)" to --accumulation--;

line 36, change "(A) accumulated (ion)" to --Accumulation--.

Col. 12, line 61, "$F_2$" should be --$f_\omega$--.

Col. 14, line 18, "executing" should be --obtaining--;

line 37, "whereof" should be --whereby--.

Signed and Sealed this

Fifteenth Day of November, 1988

Attest:

DONALD J. QUIGG

Attesting Officer      Commissioner of Patents and Trademarks